United States Patent
Sannino et al.

(10) Patent No.: US 8,658,147 B2
(45) Date of Patent: Feb. 25, 2014

(54) POLYMER HYDROGELS AND METHODS OF PREPARATION THEREOF

(75) Inventors: Alessandro Sannino, Lecce (IT); Luigi Ambrosio, Ottaviano (IT); Luigi Nicolais, Ercolano (IT); Christian Demitri, San Pietro In Lama (IT)

(73) Assignee: Gelesis LLC, Boston, MA (US)

( * ) Notice: Subject to any disclaimer, the term of this patent is extended or adjusted under 35 U.S.C. 154(b) by 355 days.

(21) Appl. No.: 12/703,286

(22) Filed: Feb. 10, 2010

(65) Prior Publication Data

US 2010/0234233 A1 Sep. 16, 2010

Related U.S. Application Data

(63) Continuation of application No. PCT/EP2008/006582, filed on Aug. 8, 2008, and a continuation-in-part of application No. PCT/IT2007/000584, filed on Aug. 10, 2007.

(51) Int. Cl.
| | |
|---|---|
| A61K 31/74 | (2006.01) |
| C08B 3/00 | (2006.01) |
| C08B 37/00 | (2006.01) |
| C08G 63/48 | (2006.01) |
| C08G 63/91 | (2006.01) |

(52) U.S. Cl.
USPC .......... 424/78.01; 536/63; 524/916; 514/911; 525/54.3

(58) Field of Classification Search
USPC ............ 524/916; 536/63; 525/54.3; 514/911; 424/78.01
See application file for complete search history.

(56) References Cited

U.S. PATENT DOCUMENTS

| | | | |
|---|---|---|---|
| 3,526,048 A | | 9/1970 | Rowland et al. |
| 5,047,513 A | * | 9/1991 | Dobeli et al. .................. 530/412 |
| 5,137,537 A | | 8/1992 | Herron et al. |
| 5,247,072 A | | 9/1993 | Ning et al. |
| 5,415,864 A | | 5/1995 | Kopecek et al. |
| 5,550,189 A | * | 8/1996 | Qin et al. ...................... 525/54.3 |
| 5,736,595 A | * | 4/1998 | Gunther et al. ................. 524/45 |
| 5,792,855 A | | 8/1998 | Yonemura et al. |
| 5,800,418 A | | 9/1998 | Ahr |
| 5,873,979 A | | 2/1999 | Naieni |
| 6,271,278 B1 | | 8/2001 | Park et al. |

(Continued)

FOREIGN PATENT DOCUMENTS

| | | |
|---|---|---|
| DD | 212 969 | 8/1984 |
| DE | 196 54 745 A1 | 7/1998 |

(Continued)

OTHER PUBLICATIONS

Sannino et al. (Journal of Applied Polymer Science, vol. 90, 168-174, 2003).*

(Continued)

*Primary Examiner* — Liam Heincer
(74) *Attorney, Agent, or Firm* — Edgar W. Harlan; Carolyn S. Elmore, Esq.; Elmore Patent Law Group, P.C.

(57) ABSTRACT

The invention relates to a method for the preparation of a polymer hydrogel, comprising cross-linking a precursor comprising a hydrophilic polymer optionally in combination with a second hydrophilic polymer, using a polycarboxylic acid as the cross-linking agent. The invention further concerns the polymer hydrogel obtainable by the method of the invention and the use thereof in a number of different applications.

20 Claims, 2 Drawing Sheets

Effect of superabsorbent polymer hydrogel (SAP) on food intake in rats

(56) References Cited

U.S. PATENT DOCUMENTS

| | | | |
|---|---|---|---|
| 6,387,978 B2* | 5/2002 | Ronan et al. | 523/113 |
| 6,471,824 B1 | 10/2002 | Jewell | |
| 6,630,422 B1 | 10/2003 | Sannino et al. | |
| 6,765,042 B1* | 7/2004 | Thornton et al. | 523/400 |
| 6,943,211 B1* | 9/2005 | Hubbell et al. | 524/556 |
| 7,071,327 B2 | 7/2006 | Mensitieri et al. | |
| 2001/0002411 A1* | 5/2001 | Ronan et al. | 523/113 |
| 2001/0006677 A1 | 7/2001 | McGinity et al. | |
| 2003/0027787 A1* | 2/2003 | Couture et al. | 514/54 |
| 2003/0144642 A1* | 7/2003 | Dopps et al. | 604/368 |
| 2004/0236016 A1* | 11/2004 | Thornton et al. | 525/54.3 |
| 2005/0100603 A1 | 5/2005 | Sako et al. | |
| 2005/0118326 A1 | 6/2005 | Anfinsen et al. | |
| 2005/0143571 A1 | 6/2005 | Stoyanov et al. | |
| 2006/0102483 A1 | 5/2006 | Chuang et al. | |
| 2006/0142478 A1* | 6/2006 | Luo et al. | 525/54.1 |
| 2006/0142480 A1* | 6/2006 | Luo et al. | 525/54.2 |
| 2008/0009616 A1* | 1/2008 | Frank et al. | 536/123.1 |
| 2008/0095911 A1 | 4/2008 | Adams et al. | |
| 2008/0147026 A1* | 6/2008 | Qin et al. | 604/358 |
| 2008/0166410 A1* | 7/2008 | Funk et al. | 424/487 |
| 2008/0184939 A1* | 8/2008 | Fritter et al. | 119/173 |
| 2008/0227944 A1 | 9/2008 | Ambrosio et al. | |
| 2008/0241094 A1 | 10/2008 | Burnett et al. | |
| 2009/0099541 A1* | 4/2009 | Qin et al. | 604/376 |
| 2009/0311235 A1 | 12/2009 | Elenko et al. | |
| 2009/0324537 A1 | 12/2009 | Bucevschi et al. | |
| 2012/0052151 A1 | 3/2012 | Sannino et al. | |

FOREIGN PATENT DOCUMENTS

| | | |
|---|---|---|
| JP | 07-082301 | 3/1995 |
| JP | 2004-010634 A | 1/2004 |
| JP | 2008-285611 A | 11/2008 |
| WO | 9602276 A2 | 2/1996 |
| WO | 9926670 A1 | 6/1999 |
| WO | 00/32064 A1 | 6/2000 |
| WO | 0187365 A2 | 11/2001 |
| WO | 2006070337 A2 | 7/2006 |
| WO | 2007112436 A2 | 10/2007 |
| WO | 2007115169 A2 | 10/2007 |

OTHER PUBLICATIONS

Demitri, C., et al., "Novel Superabsorbent Cellulose-Based Hydrogels Crosslinked with Citric Acid," Journal of Applied Polymer Science, 110:2453-2460 (2008).

Esposito, F., et al., "Water Sorption in Cellulose-Based Hydrogels," Journal of Applied Polymer Science, 60:2403-2407, 1996.

International Search Report for PCT/EP2008/006582, dated Apr. 3, 2009.

International Search Report for PCT/IT2007/000584, dated Aug. 5, 2008.

Anbergen, et al., "Elasticity and swelling behaviour of chemically crosslinked cellulose ethers in aqueous systems," Polymer, 31:1854-1858, 1990.

Sannino, A., et al, "Biodegradable-Cellulose-based Hydrogels: Design and Applications," Materials, 2:353-373, 2009.

Qiu, et al., "Effect of activated carbon on the properties of carboxymethylcellulose/activated carbon hybrid hydrogels synthesized by γ-radiation technique", Carbohydrate Polymers, 70:236-242, 2007.

Ogushi, et al., "Synthesis of Enzymatically-Gellable Carboxymethylcellulose for Biomedical Applications," Journal of Bioscience and Bioengineering, 104(1):30-33, 2007.

Liu, et al., "Radiation crosslinking of CMC-Na at low dose and its application as substitute for hydrogel," Radiation Physics and Chemistry, 72:635-638, 2005.

Liu, et al., "Radiation preparation and swelling behavior of sodium carboxymethyl cellulose hydrogels," Radiation Physics and Chemistry, 63:525-528, 2002.

Gorgieva, et al., "Synthesis and application of new temperature-responsive hydrogels based on carboxymethyl and hydroxyethyl cellulose derivatives for the functional finishing of cotton knitwear," Carbohydrate Polymers, 85:664-673, 2011.

Ito, "The prevention of peritoneal adhesions by in situ cross-linking hydrogels of hyaluronic acid and cellulose derivatives," Biomaterials, 28:975-983, 2007.

Chang, et al., "Superabsorbent hydrogels and based on cellulose for smart swelling and controllable delivery," European Polymer Journal, 46:92-100, 2010.

Chang, et al., "Structure and properties of hydrogels prepared from cellulose in NaOH/urea aqueous solutions," Carbohydrate Polymers, 82:122-127, 2010.

Esposito, et al., "Response of intestinal cells and macrophages to an orally administered cellulose-PEG based polymer as a potential treatment for intractable edemas," Biomaterials, 26:4101-4110, 2005.

Sannino, et al., "Cellulose-based hydrogels as body water retainers," J. Mater Sci: Mat in Med., 11:247-253, 2000.

Sannino, et al., "Spin Coating Cellulose Derivatives on Quartz Crystal Microbalance Plates to Obtain Hydrogel-Based Fast Sensors and Actuators," Journal of Applied Polymer Sci., 106:3040-3050, 2007.

Sannino, et al., "Concurrent effect of microporosity and chemical structure on the equilibrium sorption properties of cellulose-based hydrogels," Polymer, 46:4676-4685, 2005.

Sannino, et al., "Water and Synthetic Urine Sorption Capacity of Cellulose-Based Hydrogels under a Compressive Stress Field," Journal of Applied Polymer Science, 91:3791-3796, 2004.

Casciaro, et al., "Full experimental modelling of a liver tissue mimicking phantom for medical ultrasound studies employing different hydrogels," J. Mater Sci: Mater Med, 20:983-989, 2009.

Sannino, et al., "Designing microporous macromolecular hydrogels for biomedical applications: a comparison between two techniques," Composites Science and Technology, 63:2411-2416, 2003.

Lionetto, et al., "Ultrasonic monitoring of the network formation in superabsorbent cellulose based hydrogels," Polymer, 46:1796-1803, 2005.

Sannino, et al., "Development and Characterization of Cellulose-Based Hydrogels for Use as Dietary Bulking Agents," Journal of Applied Polymer Science, 115:1438-1444, 2010.

Marci, et al., "Environmentally sustainable production of cellulose-based superabsorbent hydrogels," Green Chem., 8:439-444, 2006.

Sannino, et al., "A Cellulose-Based Hydrogel as a Potential Bulking Agent for Hypocaloric Diets: An In Vitro Biocompatibility Study on Rat Intestine," Journal of Applied Polymer Science, 102:1524-1530, 2006.

Sannino, et al., "Crosslinking of cellulose derivatives and hyaluronic acid with water-soluble carbodiimide," Polymer, 46:11206-11212, 2005.

Sannino, et al., "Cellulose Derivative-Hyaluronic Acid-Based Microporous Hydrogels Cross-Linked through Divinyl Sulfone (DVS) to Modulate Equilibrium Sorption Capacity and Network Stability," Biomacromolecules, 5:92-96, 2004.

Sannino, et al., "Biomedical application of a superabsorbent hydrogel for body water elimination in the treatment of edemas," J. Biomed. Mater Res., 67A:1016-1024, 2003.

Casciaro, et al., "Experimental investigation and theoretical modelling of the nonlinear acoustical behaviour of a liver tissue and comparison with a tissue mimicking hydrogel," J. Mater Sci: Mater Med, 19:899-906, 2008.

Demitri, et al., "Hydrogel Based Tissue Mimicking Phantom for In-Vitro Ultrasound Contrast Agents Studies", J. Biomed Mater Res Part B: Appl Biomater, 87B:338-345, 2008.

Lenzi, et al., "Probing the degree of crosslinking of a cellulose based superabsorbing hydrogel through traditional and NMR techniques," Polymer, 44:1577-1588, 2003.

Capitani, et al., "13C Solid-State NMR Determination of Cross-Linking Degree in Superabsorbing Cellulose-Based Networks," Macromolecules, 33:430-437, 2000.

Coma, et al., "Film properties from crosslinking of cellulosic derivatives with a polyfunctional carboxylic acid," Carbohydrate Polymers, 51:265-271, 2003.

(56) References Cited

OTHER PUBLICATIONS

Xie, et al., "Development and Physicochemical Characterization of New Resistant Citrate Starch from Difference Corn Starches," Starch, 56:364-370, 2004.

* cited by examiner

POLYMER HYDROGELS AND METHODS OF PREPARATION THEREOF

BACKGROUND OF THE INVENTION

The present invention relates to polymer hydrogels and methods of preparation thereof.

Polymer hydrogels are cross-linked hydrophilic polymers which are capable of absorbing high amounts of water. In particular, cross-linked polymer hydrogels capable of absorbing an amount of water in excess of 10 times their dry weight are defined as "superabsorbent". Some of these materials are even capable of absorbing over 1 liter of water per gram of dry polymer.

The cross-links or cross-linking knots, i.e. the physical or chemical bonds between the macromolecular chains forming the polymer hydrogel network, guarantee the structural integrity of the polymer-liquid system, on the one hand preventing the complete solubilisation of the polymer, and on the other hand allowing the retention of the aqueous phase within the molecular mesh.

The superabsorbent polymer hydrogels which are currently available on the market are characterised not only by their marked absorbent properties, but also by their biocompatibility, which is probably due to the high water content, and, above all, by the possibility of adjusting their absorption properties according to the external stimuli. Consequently, such polymer hydrogels may be used as intelligent materials, for example for the manufacture of sensors or actuators for a number of industrial applications. Besides the usual applications as absorbent cores in the field of personal hygiene absorbent products, there are more recent and innovative applications such as for example in the biomedical field, for the development of controlled release drug formulations, artificial muscles, sensors, etc., and in agriculture and horticulture, for example in devices for the controlled release of water and nutrients in arid soils.

However, the superabsorbent polymer hydrogels currently available are almost exclusively acrylic-based products, and hence not biodegradable.

Given the growing interest in environmental protection issues, over recent years a vast amount of interest has been focussed on the development of superabsorbent materials based on biodegradable polymers, having properties which are similar to those of the traditional superabsorbent polyacrylics.

Examples of biodegradable polymers used to obtain superabsorbent polymer hydrogels are starch and cellulose derivatives.

In 1990 Anbergen and Oppermann [1] proposed a method for the synthesis of a superabsorbent material made entirely from cellulose derivatives. In particular, they used hydroxyethylcellulose (HEC) and a carboxymethylcellulose sodium salt (CMCNa), chemically cross-linked in a basic solution with divinylsulphone. However, the absorption properties of such materials are not high compared to those of the acrylic-based superabsorbent materials.

In 1996 Esposito and co-workers [2], studying the synthetic process proposed by Anbergen and Opperman, developed a method for increasing the absorption properties of the gel, acting mainly on the physical properties of the material. The basic idea was the induction of microporosity into the polymer structure, so as to promote absorption and retention of water by capillarity. Said microporosity was induced during the drying step, which was carried out by phase inversion in a nonsolvent for the polymer, and the absorption properties of the material thus obtained were markedly superior to those of the air-dried gel.

CMCNa may be chemically cross-linked with any reagent which is bifunctional with respect to cellulose. Besides the divinylsulphone used in the synthetic process according to Anbergen and Opperman, epichlorohydrin, formaldehyde and various diepoxides have also been used as cross-linking agents. However, such compounds are highly toxic in their unreacted states [3]. Some carbodiimides are known amongst the unconventional cross-linking agents. Particularly, the use of carbodiimides in order to cross-link salified or non-salified carboxymethylcellulose (CMC) was described in [4]. Carbodiimides induce the formation of ester bonds between cellulose macromolecules without participating in the bonds themselves, instead giving rise to a urea derivative having very low toxicity [5]. A superabsorbent polymer hydrogel obtained by cross-linking carboxymethylcellulose sodium salt and hydroxyethylcellulose with carbodiimide as the cross-linking agent is disclosed in the international patent application WO 2006/070337 [6].

However, the carbodiimide used as a cross-linking agent in WO 2006/070337 has the disadvantage of being extremely expensive. Moreover, during the cross-linking reaction with CMCNa, this substance turns into a slightly toxic urea derivative, which must be removed during the washing step, thereby further increasing the costs and the complexity of the production process. These drawbacks are extremely unfavourable, particularly in connection with those applications which require large scale production of the polymer hydrogels and which, consequently, involve high costs both with respect to the purchase of the starting materials and with respect to the disposal of the toxic substances which are produced during synthesis.

Furthermore, the formation of substances having a certain degree of toxicity, although very low, is a key factor for ruling out the possibility of using such polymers in biomedical and pharmaceutical applications.

SUMMARY OF THE INVENTION

The object of the present invention is to provide polymer hydrogels which overcome the above-mentioned disadvantages associated with the use of carbodiimide as a cross-linking agent.

These and other objects are achieved by the polymer hydrogels of the invention and the method of preparation thereof as defined herein. The polymer hydrogels of the invention are based on the use of a polycarboxylic acid, such as citric acid, as the cross-linking agent, and in preferred embodiments, also include the use of a molecular spacer.

The invention relates, in part, to the discovery that the cross-linking of soluble cellulose derivatives with citric acid (3-carboxy-3-hydroxy-1,5-pentanedioic acid; hereinafter designated "CA") results in the formation of polymer hydrogels and superabsorbent polymer hydrogels. CA is naturally occurring, non-toxic and available on the market at low cost. Although CA has been reported as a cross-linking agent for polymers such as cellulose, hydroxypropylmethylcellulose and starch, in textile and food applications [7-11], in these applications CA is used to cross-link and further stabilize insoluble fibers, to provide a fabric with enhanced resiliency and mechanical properties. However, the use of CA to cross-link carboxymethylcellulose or other soluble hydrophilic polymers for preparing polymer hydrogels and superabsorbent polymer hydrogels has not been previously disclosed.

The method of preparing a polymer hydrogel according to the present invention comprises the step of cross-linking an aqueous solution comprising a hydrophilic polymer with a polycarboxylic acid, optionally in the presence of a compound which functions as a molecular spacer.

In one embodiment, the aqueous solution comprises two or more hydrophilic polymers, such as, for example, hydroxylated polymers. For example, the aqueous solution can comprise a first hydrophilic polymer and a second hydrophilic polymer, which can be present in the same or different amounts on a weight basis. In one embodiment, the first hydrophilic polymer is an ionic polymer and the second polymer is a nonionic polymer.

In one preferred embodiment, the invention provides a method for preparing a polymer hydrogel, comprising the steps of (a) providing an aqueous solution of carboxymethylcellulose, hydroxyethylcellulose, citric acid and a molecular spacer; (b) heating the aqueous solution, thereby evaporating the water and cross-linking the carboxymethylcellulose and hydroxyethylcellulose to form a polymer hydrogel material; (c) washing the polymer hydrogel material with water or a polar organic solvent to form a washed polymer hydrogel; (d) immersing the washed polymer hydrogel in a cellulose nonsolvent, thereby producing a dried polymer hydrogel.

In yet another embodiment, the present invention provides polymer hydrogels, such as superabsorbent polymer hydrogels, which can be prepared using the methods of the invention. Such polymer hydrogels comprise at least one hydrophilic polymer cross-linked with a polycarboxylic acid. Further, the invention includes articles of manufacture which comprise such polymer hydrogels.

DETAILED DESCRIPTION OF THE INVENTION

Figure 1:
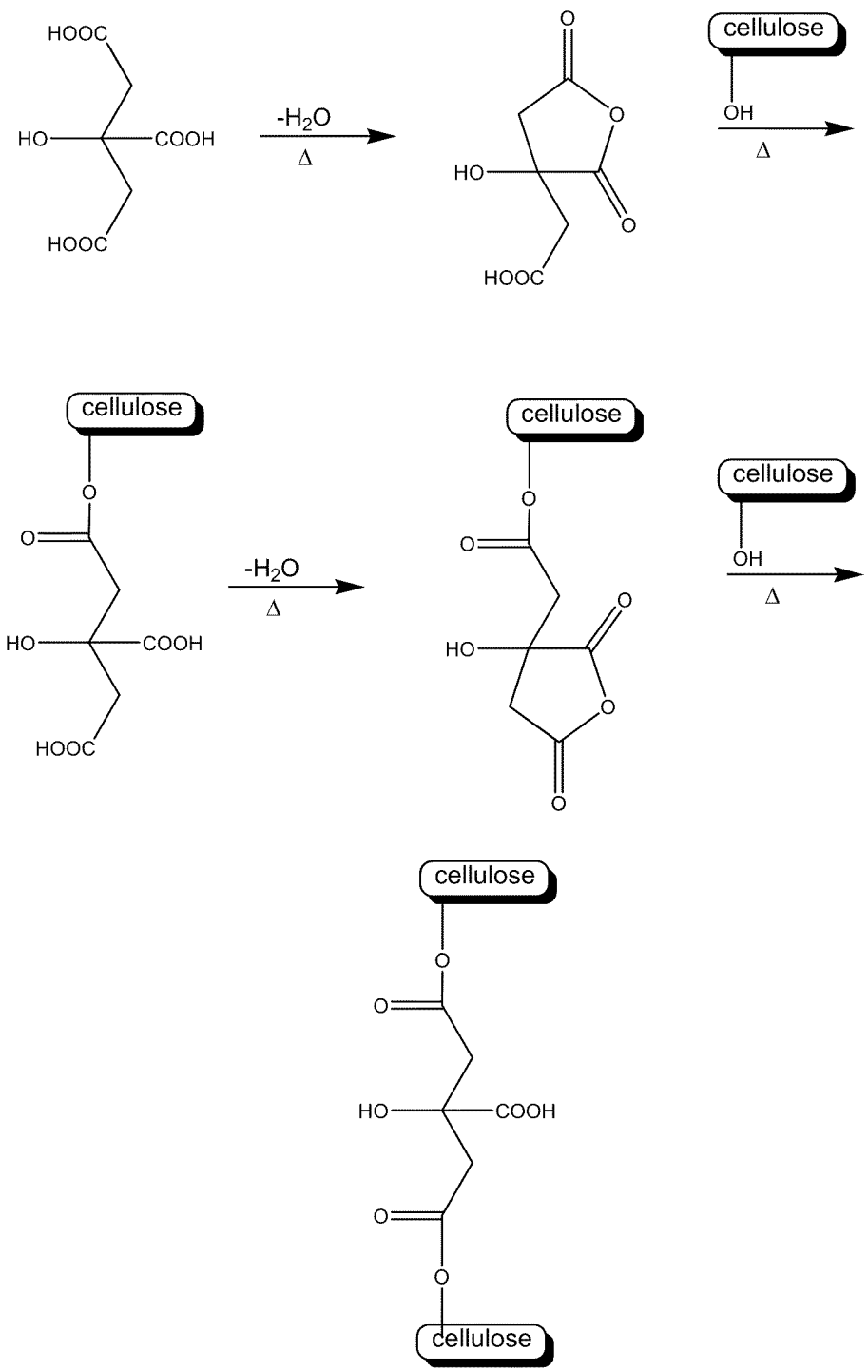
FIG. 1 illustrates the proposed mechanism of polymer cross-linking by citric acid.

The present invention provides polymer hydrogels, methods of preparing the polymer hydrogels, methods of use of the polymer hydrogels and articles of manufacture comprising the polymer hydrogels.

The method of preparing a polymer hydrogel of the present invention comprises the step of cross-linking an aqueous solution comprising a hydrophilic polymer with a polycarboxylic acid, thereby producing the polymer hydrogel. In some embodiments, the aqueous solution comprises two or more hydrophilic polymers. For example, the aqueous solution can comprise a first hydrophilic polymer and a second hydrophilic polymer, which can be present in the same or different amounts on a weight basis. In preferred embodiments, the first hydrophilic polymer is an ionic polymer and the second polymer is a nonionic polymer.

The cross-linking reaction is preferably conducted at elevated temperature, for example, at a temperature greater than room temperature (25° C.). For example, the reaction can be conducted at a temperature from about 30° C. to about 150° C., preferably from about 50° C. to about 120° C. In one embodiment, while the cross-linking reaction is conducted at elevated temperature, the reaction solution is concentrated by removal of water. The removal of water can be accomplished, for example, by evaporation. In one embodiment, a fraction of the water is removed. In another embodiment, substantially all of the water is removed, thereby producing a dry residue. Optionally, the reaction mixture is maintained at elevated temperature for a period of time following removal of water to dryness.

As used herein, the term "hydrophilic polymer" refers to a polymer which is substantially water-soluble and, preferably, includes monomeric units which are hydroxylated. A hydrophilic polymer can be a homopolymer, which includes only one repeating monomeric unit, or a copolymer, comprising two or more different repeating monomeric units. In a preferred embodiment, the hydrophilic polymer is hydroxylated, such as polyallyl alcohol, polyvinyl alcohol or a polysaccharide. Examples of suitable polysaccharides include substituted celluloses, substituted dextrans, starches and substituted starches, glycosaminoglycans, chitosan and alginates.

Polysaccharides which can be used include alkylcelluloses, such as $C_1$-$C_6$-alkylcelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, ethylhydroxyethylcellulose and carboxymethylcellulose; starches, such as corn starch, hydroxypropylstarch and carboxymethylstarch; substituted dextrans, such as dextran sulfate, dextran phosphate and diethylaminodextran; glycosaminoglycans, including heparin, hyaluronan, chondroitin, chondroitin sulfate and heparan sulfate; and polyuronic acids, such as polyglucuronic acid, polymanuronic acid, polygalacturonic acid and polyarabinic acid.

As used herein, the term "ionic polymer" refers to a polymer comprising monomeric units having an acidic functional group, such as a carboxyl, sulfate, sulfonate, phosphate or phosphonate group, or a basic functional group, such as an amino, substituted amino or guanidyl group. When in aqueous solution at a suitable pH range, an ionic polymer comprising acidic functional groups will be a polyanion, and such a polymer is referred to herein as an "anionic polymer". Likewise, in aqueous solution at a suitable pH range, an ionic polymer comprising basic functional groups will be a polycation. Such a polymer is referred to herein as a "cationic polymer". As used herein, the terms ionic polymer, anionic polymer and cationic polymer refer to hydrophilic polymers in which the acidic or basic functional groups are not charged, as well as polymers in which some or all of the acidic or basic functional groups are charged, in combination with a suitable counterion. Suitable anionic polymers include alginate, dextran sulfate, carboxymethylcellulose, hyaluronic acid, polyglucuronic acid, polymanuronic acid, polygalacturonic acid, polyarabinic acid; chrondroitin sulfate and dextran phosphate. Suitable cationic polymers include chitosan and dimethylaminodextran. A preferred ionic polymer is carboxymethylcellulose, which can be used in the acid form, or as a salt with a suitable cation, such as sodium or potassium.

The term "nonionic polymer", as used herein, refers to a hydrophilic polymer which does not comprise monomeric units having ionizable functional groups, such as acidic or basic groups. Such a polymer will be uncharged in aqueous solution. Examples of suitable nonionic polymers for use in the present method are polyallylalcohol, polyvinylalcohol, starches, such as corn starch and hydroxypropylstarch, alkylcelluloses, such as $C_1$-$C_6$-alkylcelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, and ethylhydroxyethylcellulose.

As used herein, the term "polycarboxylic acid" refers to an organic acid having two or more carboxylic acid functional groups, such as dicarboxylic acids, tricarboxylic acids and tetracarboxylic acids, and also includes the anhydride forms of such organic acids. Dicarboxylic acids include oxalic acid, malonic acid, maleic acid, malic acid, succinic acid, glutaric acid, adipic acid, pimelic acid, suberic acid, azelaic acid, sebacic acid, phthalic acid, o-phthalic acid, isophthalic acid, m-phthalic acid, and terephthalic acid. Preferred dicarboxylic acids include $C_4$-$C_{12}$-dicarboxylic acids. Suitable tricarboxylic acids include citric acid, isocitric acid, aconitic acid, and propane-1,2,3-tricarboxylic acid. Suitable tetracarboxylic acids include pyromellitic acid, 2,3,3',4'-biphenyltetracarboxylic acid, 3,3',4,4'-tetracarboxydiphenylether, 2,3',3,4'-tetracarboxydiphenylether, 3,3',4,4'-benzophenonetetracarboxylic acid, 2,3,6,7-tetracarboxynaphthalene, 1,4,5,7-tetracarboxynaphthalene, 1,4,5,6-tetracarboxynaphthalene, 3,3',4,4'-tetracarboxydiphenylmethane, 2,2-bis(3,4-dicarboxyphenyl)propane, butanetetracarboxylic acid, and cyclopentanetetracarboxylic acid. A particularly preferred polycarboxylic acid is citric acid.

The method can further include the steps of purifying the polymer hydrogel, for example, by washing the polymer hydrogel in a polar solvent, such as water, a polar organic solvent, for example, an alcohol, such as methanol or ethanol, or a combination thereof. The polymer hydrogel immersed in the polar solvent swells and releases any component, such as by-products or unreacted polycarboxylic acid that was not incorporated into the polymer network. Water is preferred as the polar solvent, distilled water is still more preferred. The volume of water required during this step to reach the maximum swelling degree of the gel, is approximately 10- to 20-fold greater than the initial volume of the gel itself. Taking into account the substantial amounts of water which would be involved during this step on an industrial scale, as well as the disposal and/or recycling of the washes, the importance of avoiding the presence of any toxic by-products in the synthetic process becomes evident. The polymer hydrogel washing step may be repeated more than once, optionally changing the polar solvent employed. For example, the polymer hydrogel can be washed with methanol or ethanol followed by distilled water, with these two steps optionally repeated one or more times.

The method can further include drying of the polymer hydrogel. The drying step is carried out by immersing the fully swollen polymer hydrogel in a cellulose nonsolvent, a process known as phase inversion. Suitable cellulose nonsolvents include, for example, acetone and ethanol. Drying the polymer hydrogel by phase inversion results in a final microporous structure which improves the absorption properties of the polymer hydrogel by capillarity. Moreover, if the porosity is interconnected or open, i.e. the micropores communicate with one another, the absorption/desorption kinetics of the gel will be improved as well. When a completely or partially swollen gel is immersed into a nonsolvent, the gel undergoes phase inversion with the expulsion of water, until the gel precipitates in the form of a vitreous solid as white coloured particles. Various rinses in the nonsolvent may be necessary in order to obtain the dried gel in a short period of time. For example, when the swollen polymer hydrogel is immersed in acetone as the non-solvent, a water/acetone mixture is formed which increases in water content as the polymer hydrogel dries; at a certain acetone/water concentration, for example, about 55% in acetone, water is no longer able to exit from the polymer hydrogel, and thus fresh acetone has to be added to the polymer hydrogel to proceed with the drying process. The higher the acetone/water ratio during drying, the faster is the drying process. Pore dimensions are affected by the rate of the drying process and the initial dimensions of the polymer hydrogel particles: larger particles and a faster process tend to increase the pore dimensions; pore dimensions in the microscale range are preferred, as pores in this size range exhibit a strong capillary effect, resulting in the higher sorption and water retention capacity.

The polymer hydrogels of the invention can also be dried by another process, such as air drying, freeze drying or oven drying. These drying methods can be used alone, in combination, or in combination with the non-solvent drying step described above. For example, the polymer hydrogel can be dried in a non-solvent, followed by air drying, freeze drying, oven drying, or a combination thereof to eliminate any residual traces of nonsolvent. Oven drying can be carried out at a temperature of e.g. approximately 30-45° C. until the residual nonsolvent is completely removed. The washed and dried polymer hydrogel can then be used as is, or can be milled to produce polymer hydrogel particles of a desired size.

The cross-linking solution can optionally include a compound which serves as a molecular spacer. A "molecular spacer", as this term is used herein, is a polyhydroxylated compound which, although not taking part in the reaction resulting in the formation of the cross-linked polymer hydrogel network to a significant extent, results in a polymer hydrogel with an increased absorption capacity. Although in certain cases the molecular spacer may participate in the cross-linking reaction to a small extent, it is believed that molecular spacers function by sterically blocking access to the polymer chains, thereby increasing the average distance between the polymer chains. Cross-linking, therefore, can occur at sites which are not close together, thereby enhancing the ability of the polymer network to expand so as to greatly increase the polymer hydrogel absorption properties. Suitable compounds for use as molecular spacers in the methods of the present invention include monosaccharides, disaccharides and sugar alcohols, including sucrose, sorbitol, plant glycerol, mannitol, trehalose, lactose, maltose, erythritol, xylitol, lactitol, maltitol, arabitol, glycerol, isomalt and cellobiose. The molecular spacer is preferably included in the cross-linking solution in the amount of about 0.5% to about 10% by weight relative to the solvent, more preferably about 2% to about 8% and more preferably about 4%.

According to a preferred embodiment of the invention, the molecular spacer used to synthesise the polymer hydrogel is selected from the group consisting of sorbitol, sucrose and plant glycerol.

According to a particularly preferred embodiment of the method of the invention, sorbitol is used as the molecular spacer, at a concentration within the range of 0.5 to 10% by weight referred to the weight of water, preferably within the range of 2 to 8% by weight referred to the weight of water, still more preferably at a concentration of 4% by weight referred to the weight of water.

In one embodiment, the aqueous solution includes an ionic polymer, preferably an anionic polymer, and most preferably, carboxymethylcellulose. In a particularly preferred embodiment the anionic polymer is carboxymethylcellulose and the polycarboxylic acid is citric acid.

In another embodiment, the aqueous solution includes an ionic polymer and a non-ionic polymer. The ionic polymer is preferably an anionic polymer, and most preferably, carboxymethylcellulose. The non-ionic polymer is preferably a substituted cellulose, more preferably a hydroxyalkylcellulose or a hydroxyalkyl alkylcellulose, and most preferably hydroxyethylcellulose ("HEC"). The preferred polycarboxylic acid is citric acid.

The weight ratios of the ionic and non-ionic polymers (ionic:non-ionic) can range from about 1:10 to about 10:1, preferably from about 1:5 to about 5:1. In preferred embodiments, the weight ratio is greater than 1:1, for example, from about 2 to about 5. In a particularly preferred embodiment, the ionic polymer is carboxymethycellulose, the non-ionic polymer is hydroxyethylcellulose, and the weight ratio (ionic:nonionic) is about 3:1.

In a preferred embodiment of the method of the invention, which results in the formation of superabsorbent polymer hydrogels having a particularly high swelling ratio (SR), the total precursor concentration in the aqueous solution is of at least 2% by weight referred to the weight of the water of the starting aqueous solution, and the amount of the cross-linking agent is between about 1% and about 5% by weight referred to the weight of the precursor. In the present description, the term "precursor" indicates the hydrophilic polymer(s) used as the precursors for the formation of the polymer hydrogel polymer network, for example, in certain embodiments the "weight of the precursor" is the weight of CMCNa used or the combined weights of CMCNa and HEC used. The aqueous solution preferably includes sorbitol in an amount of about 4% by weight relative to the weight of water.

The swelling ratio (SR) is a measure of the ability of the polymer hydrogel to absorb water. SR is obtained through swelling measurements at the equilibrium (using, for example, a Sartorius micro scale with a sensitivity of $10^{-5}$) and it is calculated with the following formula:

$$SR=(W_s-W_d)/W_d$$

wherein $W_s$ is the weight of the polymer hydrogel after immersion in distilled water for 24 hours, and $W_d$ is the weight of the polymer hydrogel before immersion, the polymer hydrogel having been previously dried in order to remove any residual water.

According to the preparation method of the invention, in this embodiment, the cross-linking reaction is preferably carried out at a temperature between about 60° C. and 120° C. Varying the temperature during this stage of the process will enable one to increase or decrease the cross-linking degree of the polymer network. A cross-linking temperature of about 80° C. is preferred.

One particularly preferred embodiment of the method of the invention comprises the following steps: Step 1, the hydrophilic polymer(s), the carboxylic acid and, optionally, the molecular spacer are dissolved in water at room temperature; Step 2, the water is removed from the solution at 40° C. over a two-day period; Step 3, the product of Step 2 is heated to 80° C. for 10 hours to induce the cross-linking reaction and form a polymer hydrogel; Step 4, the polymer hydrogel is washed three times with water over 24 hours; Step 5, the washed polymer hydrogel is immersed in acetone for 24 hours to remove water; Step 6, the polymer hydrogel is further dried in an oven at 45° C. for 5 hours; and Step 7, the dried polymer hydrogel is milled to provide polymer hydrogel particles.

The present invention also provides polymer hydrogels which can be prepared using the methods of the invention. Such polymer hydrogels comprise a hydrophilic polymer cross-linked with a polycarboxylic acid. In other embodiments, the polymer hydrogels of the invention include at least two hydrophilic polymers cross-linked by a polycarboxylic acid. In one preferred embodiment, the polymer hydrogel comprises an ionic polymer and a non-ionic polymer and a polycarboxylic acid, preferably a $C_4$ to $C_{12}$-dicarboxylic acid, a tricarboxylic acid or a tetracarboxylic acid, where the polycarboxylic acid cross-links the ionic polymer and the non-ionic polymer. The weight ratio of ionic polymer to non-ionic polymer is preferably from about 1:5 to about 5:1, more preferably from about 2:1 to about 5:1, and most preferably about 3:1. In one particularly preferred embodiment, the ionic polymer is carboxymethylcellulose, the non-ionic polymer is hydroxyethylcellulose and the polycarboxylic acid is citric acid. In another preferred embodiment, the polymer hydrogel comprises an ionic polymer, for example, an anionic polymer or a cationic polymer. More preferably, the ionic polymer is carboxymethylcellulose or a salt thereof, such as sodium carboxymethylcellulose. In another particularly preferred embodiment, the polymer hydrogel comprises carboxymethylcellulose cross-linked with citric acid.

The polymer hydrogels of the invention have swelling ratios of at least about 5. Preferably, the polymer hydrogels of the invention are superabsorbent polymer hydrogels, for example, polymer hydrogels having an SR of at least 10. In preferred embodiments, the polymer hydrogels of the invention have SRs at least about 20, about 30, about 40, about 50, about 60, about 70, about 80, about 90 or about 100. For example, in certain embodiments, the polymer hydrogels of the invention have SRs from about 10 to about 100, from about 20 to about 100, from about 30 to about 100, from about 40 to about 100, from about 50 to about 100, from about 60 to about 100, from about 70 to about 100, from about 80 to about 100, or from about 90 to about 100. In certain embodiments, the invention includes polymer hydrogels having SRs up to 150, 200, 250, 300, 330 or 350.

In certain embodiments, the polymer hydrogels of the invention can absorb an amount of one or more bodily fluids, such as blood, blood plasma, urine, intestinal fluid or gastric fluid, which is at least 10, 20, 30, 40, 50, 60, 70, 80, 90, or 100 times their dry weight. The ability of the polymer hydrogel to absorb bodily fluids can be tested using conventional means, including testing with samples of bodily fluids obtained from one or more subjects or with simulated bodily fluids, such as simulated urine or gastric fluid. In certain preferred embodiments, the polymer hydrogels can absorb significant amounts of a fluid prepared by combining one volume of simulated gastric fluid (SGF) with eight volumes of water. SGF can be prepared using USP Test Solutions procedures which are known in the art. In some embodiments, the polymer hydrogels of the invention can absorb at least about 10, 20, 30, 40, 50, 60, 70, 80, 90, 100 or more times their dry weight of this SGF/water mixture.

The polymer hydrogels of the invention include cross-linked polymers having varying extents of hydration. For example, the polymer hydrogels can be provided in a state of hydration ranging from a substantially dry or anhydrous state, such as a state in which from about 0% to about 5% of the polymer hydrogel by weight is water or an aqueous fluid, to states comprising a substantial amount of water or aqueous fluid, including up to a state in which the polymer hydrogel has absorbed a maximum amount of water or an aqueous fluid.

The polymer hydrogels of the invention can be used in methods for treating obesity, reducing food or calorie intake or achieving or maintaining satiety. The methods comprise the step of administering an effective amount of a polymer hydrogel of the invention to the stomach of a subject, preferably by causing the subject, such as a mammal, including a human, to ingest the polymer hydrogel. Such polymer hydrogels can be used to take up stomach volume, for example, by increasing the volume of a food bolus without adding to the calorie content of the food. The polymer hydrogel can be ingested by the subject prior to eating or in combination with food, for example, as a mixture of the polymer hydrogel with food. Upon ingestion and contact with gastric fluid or a combination of gastric fluid and water, the polymer hydrogel will swell. The polymer hydrogel can be ingested alone or in a mixture with liquid or dry food in a dry, partially swollen or fully swollen state, but is preferably ingested in a state of hydration which is significantly below its fluid capacity, more preferably the polymer hydrogel is ingested in an anhydrous state. Thus, the volume of the stomach taken up by the polymer hydrogel can be significantly greater than the volume of the polymer hydrogel ingested by the subject. The polymer hydrogels of the invention can also take up volume and/or exert pressure on the wall of the small intestine by moving from the stomach into the small intestine and swelling. Preferably, the polymer hydrogel will remain swollen in the small intestine for a period of time sufficient to inhibit the intake of food by the subject, before shrinking sufficiently for excretion from the body. The time sufficient to inhibit the intake of food by the subject will generally be the time required for the subject to eat and for the ingested food to pass through the small intestine, Such shrinking can occur, for example, by degradation through loss of cross-links, releasing fluid and decreasing in volume sufficiently for excretion from the body. Preferred polymers for use in this method exhibit pH-dependent swelling, with greater swelling observed at higher pH than at lower pH. Thus, such a polymer will not swell significantly in the stomach unless food and/or water is present to raise the pH of the stomach contents and will move into the small intestine. When ingested with food, the polymer hydrogel will initially swell in the stomach, then shrink when the stomach is emptied of food and the pH drops and then move from the stomach to the small intestine. In the higher pH environment of the small intestine the polymer hydrogel will swell, taking up volume in the small intestine and/or exerting pressure on the wall of the small intestine.

The polymer hydrogel can optionally be administered in combination with a pH modifying agent, which is an agent which alters the pH of the microenvironment of the polymer hydrogel, thereby modifying its ability to absorb fluids. For example, for polymer hydrogels comprising an anionic polymer, agents which increase the pH of the microenvironment can increase the swellability of the polymer hydrogel. Suitable pH modifying agents for use with the polymer hydrogels of the invention include buffering agents, $H_2$ blockers, proton pump inhibitors, anatacids, proteins, nutritional shakes, and combinations thereof. Suitable buffering agents and antacids include ammonium bicarbonate, sodium bicarbonate, calcium carbonate, calcium hydroxide, aluminium hydroxide, aluminium carbonate, magnesium carbonate, magnesium hydroxide, potassium bicarbonate, potassium carbonate, potassium hydroxide, sodium carbonate, sodium hydroxide and combinations thereof. Suitable $H_2$ blockers include cimetidine, ranitidine, famotidine, nizatidine and combinations thereof. Suitable proton pump inhibitors include omeprazole, lansoprazole, esorneprazole, pantoprazole, abeprazole, and combinations thereof.

The present polymer hydrogels can also be used for removing water from the gastrointestinal tract, for example, as a treatment for subjects suffering from kidney disease, including chronic and acute kidney disease, particularly subjects undergoing kidney dialysis. The polymer hydrogels can further be used to modify the fluid content in the gastrointestinal tract of a subject in need thereof, for example, for the treatment of constipation.

The invention further includes articles of manufacture which comprise the polymer hydrogels of the invention. Such articles of manufacture include articles in which polyacrylic polymer hydrogels are conventionally used, in consumer products, such as for example absorbent products for personal care (i.e., babies' napkins, sanitary towels, etc.) and in products for agriculture (e.g., devices for the controlled release of water and nutrients). The absorption properties of the polymer hydrogels of the invention, which in some embodiments depend on the amount of carboxymethylcellulose employed and which can be improved by the induction of a microporosity in the gel structure, are comparable to those of polyacrylic gels. The polymer hydrogels obtainable by the method of the present invention therefore possess mechanical properties which make them suitable for use in all of the above-mentioned fields. The present polymer hydrogels, however, have advantages over acrylic polymer hydrogels, such as biodegradability, the absence of any toxic by-products during the manufacturing process and the use of fewer and readily available reagents. Such features enable a real employment of the polymer hydrogels of the invention in the biomedical and pharmaceutical fields as well.

Thus, the scope of the present invention also includes the use of the polymer hydrogels obtainable by the method of the invention as an absorbent material in products which are capable of absorbing water and/or aqueous solutions and/or which are capable of swelling when brought into contact with water and/or an aqueous solution.

The polymer hydrogels and superabsorbent polymer hydrogels of the present invention may be used as absorbent materials in the following fields, which are provided by way of non-limiting example:

dietary supplements (for example, as the bulking agents in dietary supplements for hypocaloric diets capable of conferring a sensation of lasting satiety being retained into the stomach for a limited period of time, or as water and low molecular weight compounds supplements, such as mineral salts or vitamins, to be included into drinks in a dry or swollen form);

in agricultural products (for example, in devices for the controlled release of water and/or nutrients and/or phytochemicals, particularly for cultivation in arid, deserted areas and in all cases where it is not possible to carry out frequent irrigation; such products, mixed in a dry form with the soil in the areas surrounding the plant roots, absorb water during irrigation and are capable of retaining it, releasing it slowly in certain cases, together with the nutrients and phytochemicals useful for cultivation);

in personal hygiene and household absorbent products (such as for example, as the absorbent cores in babies' napkins, sanitary towels and the like);

in the field of toys and gadgets (such as for example in products which are capable of significantly changing their size once brought into contact with water or an aqueous solution);

in the biomedical field (for example, in biomedical and/or medical devices such as absorbent dressings for the treatment of highly exudative wounds, such as ulcers and/or burns, or in slow-release polymeric films suitable to slowly release liquids adapted for use in opthalmology); and in the body fluid management field, i.e., for controlling the amount of liquids into the organism, for example in products capable of promoting the elimination of fluids from the body, such as, for example, in the case of edema, CHF (chronic heart failure), dialysis.

The above-mentioned products, containing a polymer hydrogel of the present invention as the absorbent material, also fall within the scope of the invention.

The invention further includes the use of any of the polymer hydrogels of the invention in medicine. Such use includes the use of a polymer hydrogel in the preparation of a medicament for the treatment of obesity or any medical disorder or disease in which calorie restriction has a therapeutic, palliative or prophylactic benefit.

The following examples are provided to further illustrate the invention and are not to be construed as limiting its scope.

EXAMPLES

The materials and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, derivatives, formulations and/or methods of the invention may be made without departing from the spirit of the invention and the scope of the appended claims.

Example 1

Citric Acid Cross-Linking of Carboxymethylcellulose/Hydroxyethylcellulose Mixtures Materials CMCNa (MW 700 kDa, DS 0.9, food grade), HEC (MW 250 kDa, food grade) were purchased from Eigenmann e Veronelli S.p.A. Milano and citric acid was supplied by Dal Cin S.p.A. Sesto San Giovanni Milano and used as received.

Polymer Hydrogel Synthesis

Polymer hydrogel samples were obtained by reacting, in water, CMCNa and HEC with citric acid as a cross-linking agent according the following procedure. First, a total polymer concentration of 2% by weight of water, using a mixture of CMCNa and HEC, with weight ratio equal to 3/1 was dissolved in distilled water by stirring gently at room temperature until a clear solution was obtained. Poor cross-linking efficiency has been reported if only CMCNa is used, due both to the electrostatic repulsion between polyelectrolyte chains and to the high degree of substitution of hydroxyl groups at C6, the most reactive position [13]. CMCNa dissolution is slow at the concentration adopted; thus, first HEC was added to water till, after 5 min, a clear solution was obtained with a slight increase of viscosity; then, CMCNa was added, and the stirring was kept on till a clear solution was obtained (24 h), with a significant increase of viscosity. Finally, CA was added at different concentrations (1.75%, 2.75%, 3.75%, 10% and 20% w/w polymer) in order to obtain samples with various degrees of cross-linking. This final solution was used to mold 10 mm thick samples. All samples were first pre-dried at 30° C. for 24 h to remove absorbed water and then kept at 80° C. for the cross-linking reaction (24 h with intermediate control).

Moreover, samples containing neat HEC or neat CMCNa samples cross-linked with CA were also prepared following exactly the same experimental conditions used for HEC/CMCNa mixtures.

All samples were analyzed by FT IR measurements. Anhydride formation was detected by monitoring its characteristic stretching band in the carbonyl region at 1738 cm$^{-1}$ [14].

Swelling Ratio

Equilibrium swelling measurements for all the samples were carried out in distilled water using a Sartorius microbalance (10$^{-5}$ sensitivity). The swelling ratio was measured by weighing samples before and after their immersion in distilled water for about 24 h. The swelling ratio (SR) is defined as following:

$$SR=(W_s-W_d)/W_d$$

where $W_s$ is the weight of the swollen polymer hydrogel and $W_d$ is the weight of the dried sample [15].

Differential Scanning Calorimeter

A differential scanning calorimeter (Mettler-Toledo 822$^e$ Mettler DSC) was used for thermal analysis. The scanning temperature range and the heating rate were 10-200° C. and 5° C./min, respectively.

The adopted thermal cycle was: (1) heating 10-100° C.; (2) isotherm at 100° C. for 3 minutes; (3) cooling from 100° C. to 10° C.; (4) heating from 10° C. to 200° C.; (5) isotherm at 200° C.; (6) cooling until room temperature. An empty pan was used as a reference.

Fourier Transformed Infrared Spectroscopy

All FT IR spectra were recorded on a JASCO FT IR 660 plus spectrometer equipped with an attenuated total reflectance (ATR) crystal sampler. Film samples were used directly on a ATR crystal sampler at a resolution of 4 cm$^{-1}$, by 300 scans, at absorbance range from 4000 cm$^{-1}$ to 600 cm$^{-1}$.

Results and Discussion

A DSC thermogram of neat citric acid showed a peak at about 60° C., attributable to a water loss process associated with the dehydration leading to an anhydride. A complete degradation, starting at about 160° C., is observed in the second scan.

DSC analysis of neat CMCNa and HEC powders indicates that some water is still absorbed in the polymers. Above 100° C. a possible degradation peak of CMCNa is detected. Both CMCNa and HEC show a thermal stability below 100° C.

A film of polymer hydrogel obtained using a 3:1 ratio of CMCNa/HEC and 3.75% by weight of polymer of citric acid was analyzed by DSC after drying the sample at 30° C. for 24 h and then reduced to powder. A large endothermic peak associated to the evaporation of the water produced by the anhydrification process is evident. A small exothermic peak, attributed to esterification is superimposed on the first one. In the second heating cycle the glass transition ($T_g=38°$ C.) of the cross-linked cellulose mixture is observed.

After this preliminary DSC study, different polymer hydrogel samples were prepared according the following procedures. After mixing reagents in water, the reaction vessel was kept at 30° C. for 24 h in dry conditions to remove water. Then temperature was raised above 60° C., according with the results of the first DSC analysis, in order to obtain the citric acid anhydride. Above this limiting temperature citric anhydride is available for the cross-linking reaction with cellulose OH groups. Different reaction conditions were attempted in order to optimize the synthetic procedure, such as temperature and CA concentration as summarized in Table 1. Two different reaction temperatures for the cross-linking process, 80° C. and 120° C., were attempted. However, either to prevent degradation risks or to limit the reaction rate a temperature of 80° C. was chosen. Moreover, very high concentrations (10% and 20% by weight) of CA were initially used in order to amplify the FT IR signals associated with each chemical reaction step. First neat CMCNa and HEC were cross-linked with CA in order to investigate its reactivity with each of the polymers.

TABLE 1

| Reaction label | Initial polymer | citric acid concentration (% w/w polymer) |
|---|---|---|
| A10 | CMCNa | 10 |
| A20 | CMCNa | 20 |
| B10 | HEC | 10 |
| B20 | HEC | 20 |
| C10 | CMCNa/HEC (3/1) | 10 |
| C20 | CMCNa/HEC (3/1) | 20 |

FT IR spectra were recorded of citric acid, of the A10 reaction mixture before heating and of the A10 reaction mixture after 5 h of heating. In the CA spectrum it is possible to observe a strong C=O band centred at 1715 cm$^{-1}$ due to carboxylic acid. The FT IR spectrum of sample A10 shows a strong absorption band at 1590 cm$^{-1}$ characteristic of cellulose [16]. After heating, the absorbance band at about 1590 cm$^{-1}$ is still observed and additionally a new band at 1738 cm$^{-1}$ appears. Anhydrides display two stretching bands in the carbonyl region around 1758 cm$^{-1}$ and 1828 cm$^{-1}$. The higher frequency band is the more intense in acyclic anhydrides whereas cyclic anhydrides show the lower frequency C=O stretching band stronger than the stretching band at higher frequency [14]. The new peak observed at 1738 cm$^{-1}$ can be attributed to the characteristic stretching band of the carbonyl group at lower frequency related to anhydride formation, an intermediate reaction necessary for reaction of CA with cellulose hydroxyl groups. In contrast, the carbonyl peak expected at higher frequency is not detectable probably due to its weak intensity.

FT IR spectra were recorded of citric acid, B10 reaction mixture before heating and B10 reaction mixture after 6.5 h of heating. The HEC spectrum again shows the band at 1590 cm$^{-1}$ before and after heating while the absorbance of the carbonyl group at 1738 cm$^{-1}$ appears only after heating at 80° C. as observed for the sample A10.

Although FT IR analysis is generally considered a qualitative technique, a literature study in literature carried out by Coma and co-workers demonstrated that infrared spectroscopy could be used at first approximation for the determination of the cross-linking rate in cross-linked cellulosic derivatives [9]. Starting from this consideration, the evolution of the different reactions finally leading to cross-linking at 80° C. was monitored by recording FT IR spectra at different reaction times.

The area under the absorbance peak at 1738 cm$^{-1}$ ($A_1$) representative of the carbonyl group, was compared with the area under the reference absorbance peak at 1592 cm$^{-1}$ ($A_2$) which is invariant in all spectra. The evolution of the anhydride was evaluated as the ratio of $A_1/A_2$ as a function of the reaction time. FTIR spectra of CMCNa polymer when the reaction is performed at 80° C. with 20% CA or 10% CA both show a similar trend: the anhydride band, that is absent before heating, reaches a maximum almost immediately after the first hour, successively decreases to a minimum after 3 h, then increasing again reaching a second maximum after 5 h. Finally a slower process reduces the band area to zero after 24 h. It is worth noting that in the spectrum of the 20% CA reaction, the second maximum matches a value ($A_1/A_2$=0.10) higher than those observed in the 10% CA reaction ($A_1/A_2$=0.04).

It is assumed that the peak at around 1738 cm$^{-1}$ is due to the anhydrification process involving free CA followed by the first condensation of this anhydride with cellulose OH leading to a fast disappearance of the anhydride C=O groups. Then the carboxylate groups now linked to the polymer are able to form again an anhydride leading to an increase of the 1738 cm$^{-1}$ peak. The second reaction of this anhydride is responsible for the cross-linking, results in a new anhydride group consumption and consequent reduction of the peak at 1738 cm$^{-1}$. This second reaction is slower since it involves groups linked to large macromolecules and hence is more sterically hindered, as has also been reported for other cellulose cross-linking processes [17]. This possible reaction mechanism is confirmed by the swelling measurements.

FTIR spectra were also recorded for reactions of HEC polymer when the reaction is performed at 80° C. with either 20% CA or 10% CA. In the 10% CA case, the anhydride band intensity increases from 0 to 0.098 when the reaction time increase from 0 h to 6.5 h, but drops to 0 when the reaction time reaches 24 h. The 20% CA reaction follows exactly the same trend providing a maximum value of 0.079 at 5 h. Assuming that the cross-linking mechanism is the same as described for CMCNa, the anhydrification and esterification reactions appear superimposed in this case. Therefore, in the FTIR spectra, the HEC polymer shows a single peak. This latter result was in accordance with conclusion of Xie and co-workers [18]. They studied the degree of substitution, as evaluation of cross-linking esterification, on starch thermally reacted with CA at different reaction time and found a maximum after a few hours.

To explain the data observed in all FTIR spectra recorded after 24 hours, we supposed that in all cases the polymer is unstable when is kept in the oven for 24 hours because of unidentified secondary reactions take place modifying polymer structure that involve also ester functions. Xie and co-workers [18] work guessed that the degree of substitution reached a maximum and then decreased since dissociation of the substituents from starch occurred when the reaction time was longer than 7 h.

Finally, to complete this study, polymer mixtures of CMCNa and HEC were cross-linked. CMCNa has carboxylic acid functional groups in its structure that increase the volume variation process in solution. A preliminary attempt to follow the reaction pathway failed. Probably the reaction systems considered are too complex having many different reaction centers. FT IR spectra of C10 reaction registered before, after 8 h and after 13 h of heating were compared. Reaction sample C20 shows similar spectra. Moreover, it is worth noting that when polymer mixtures are used (C10 and C20) a broad signal appears at about 1715 cm$^{-1}$, especially when a higher CA concentration is used in the reaction. In fact, with 20% of CA the signal of CA at 1715 cm$^{-1}$ is very broad and overlapped to the polymer signal at 1590 cm$^{-1}$ then a clear band is not detectable. However, it should be pointed out a band around 1715 cm$^{-1}$ before heating. The C10 reaction mixture before heating shows a band around 1715 cm$^{-1}$ covering the absorbance region monitored previously for the other reactions (A10, A20, B10, B20); consequently a clear assignment to the carbonyl group is difficult. However, the other two spectra indicate that this band moves to higher wavenumbers during the cross-linking reaction. In particular after 8 h, the FT IR spectrum shows a broad band in the range of 1711 cm$^{-1}$-1736 cm$^{-1}$ and after 13 h this band appears more clearly as a narrow absorbance band at 1737 cm$^{-1}$, which is typical of carbonyl groups. Spectra of C20 reaction provide similar results. Although a quantitative analysis of carbonyl groups is not possible when C10 and C20 samples are cross-linked, an evaluation of the carbonyl peak similar to those observed for the reaction of the neat polymers can be assumed.

The cross-linking kinetics were also monitored studying the swelling behaviour during the reaction progress. Swelling ratio was calculated as a function of the reaction time for: (a)

CMCNa with 10% or 20% of CA concentration; (b) HEC with 10% or 20% of CA concentration; (c) the mixture of CMCNa and HEC (3/1) with 10% or 20% CA concentration; (d) the mixture of CMCNa and HEC (3/1) with 1.75%, 2.75% or 3.75% CA concentration.

The results obtained indicate that the swelling of CMCNa cross-linked with 10% of citric acid is higher than HEC with the same citric acid concentration after 24 h. When 20% of citric acid was added to the celluloses, the shape of the swelling curves are similar for HEC and CMCNa. In this case, as cross-linking proceeds the swelling of HEC based samples decreases faster than CMCNa samples indicating that a higher rate of reaction between CA and HEC. This probably occurs because HEC is less sterically hindered than CMCNa and can react more quickly than CMCNa chains. In addition in each repeating unit, HEC has more OH groups than CMCNa (3 vs 2).

The maximum swelling of CMCNa/CA sample is observed at the gelation onset, after 3 h, when the second esterification reaction, those leading to cross-linking, begins. Then as the cross-linking process increases the corresponding equilibrium water sorption decreases, confirming the results of FTIR analysis.

The same reaction mechanism can be assumed for neat HEC cross-linked with CA. However in this case the overall behaviour is slightly different as a consequence of the absence of carboxylic groups bonded to the polymer. The results of swelling experiments must be interpreted taking into account that the CA introduces the high hydrophilic carboxylic groups that are responsible of the formation of a polyelectrolyte network. Therefore the water sorption is significantly increased as carboxylic groups are linked first to the HEC chains and then to the gelled network. This effect cannot be appreciated in CMCNa polymer hydrogels since a large amount of —COOH groups, those linked to the CMCNa chains, is already bonded to the network at the onset of gelation. A similar trend is observed for the mixtures of HEC and CMCNa.

Polymer hydrogels of practical use presenting a high degree of swelling were obtained with a reduced concentration of citric acid (1.75%, 2.75%, 3.75% by weight of polymer). With a citric acid concentration of 3.75% the swelling ratio can reach 900. This 1 (1 polymer hydrogel, after swelling, is characterized by adequate stiffness and it is able to keep the same shape of the synthesis vat. Polymer hydrogels formerly synthesized [13] using divinyl sulfone, a toxic reagent, as cross-linking agents and the same ratio between CMCNa and HEC were characterized by a maximum swelling ratio of 200. In this case a higher swelling ratio is obtained using an environmentally friendly cross-linking agent. At concentrations lower than 1.75% CA, a weak cross-linking associated with insufficient mechanical property is observed.

Conclusions

This work shows for the first time that CA can be successfully used as cross-linking agent of CMCNa/HEC mixtures. As shown in FIG. 1, an esterification mechanism based on an anhydride intermediate formation is proposed to explain the reaction of cellulose polymers with CA.

The cross-linking reaction for CMCNa/HEC system was observed either by DSC or by FTIR analysis. The evolution of the different cross-linking reactions was monitored by means of FT IR spectra collected at different reaction times using an excess of citric acid. The swelling ratio, monitored at different reaction times, confirmed the reaction path figured out from FTIR analysis. An optimal degree of swelling (900) for practical applications was achieved using low CA concentrations. The polymer hydrogel obtained through the method described in this Example 1 has the great advantage to reduce primary and production costs and avoid any toxic intermediate during its synthetic process.

Example 2

Citric Acid Cross-Linking of Carboxymethylcellulose and Carboxymethylcellulose/Hydroxyethylcellulose Mixtures in the Presence of Sorbitol Materials and Methods All the materials employed were provided by Aldrich Italia and were used without any further modification. The devices used in the characterisation, in addition to the standard laboratory glassware, cupboards and counters for standard synthesis, were a scanning electron microscope (SEM) JEOL JSM-6500F, a precision $10^{-5}$ g Sartorius scale, an Isco mixer and an ARES rheometer.

The polymer hydrogels were prepared by cross-linking an aqueous solution of carboxymethylcellulose sodium salt (CMCNa) and hydroxyethylcellulose (HEC), using citric acid (CA) as the cross-linking agent and sorbitol as the molecular spacer. The composition of a gel is given by the nominal amount of the reagents in the starting solution. The parameters used to define said composition are the following:
(i) the precursor weight concentration (%)=the total mass of polymers in the solution (e.g. CMCNa+HEC) (g)×100/mass of water (g);
(ii) the CMCNa to HEC weight ratio=mass of CMCNa (g) in the solution/mass of HEC in the solution (g);
(iii) the cross-linking agent (CA) weight concentration (%)=mass of CA in the solution (g)×100/mass of the precursors in the solution (g); and
(iv) the molecular spacer (e.g. sorbitol) weight concentration (%)=mass of molecular spacer (g)×100/mass of water (g).

The laboratory tests demonstrated that a polymer concentration lower than 2% and a CA concentration lower than 1% either do not achieve cross-linking of the gel or led to the synthesis of a gel having very poor mechanical properties. On the other hand, CA concentrations higher than about 5% significantly increase the cross-linking degree and polymer stabilization, but excessively reduce the absorption properties of the superabsorbent gel.

Since CMCNa is the ionic polymer species, it is possible to achieve the desired absorption properties adjusting the weight ratio of carboxymethylcellulose sodium salt (CMCNa) to hydroxyethylcellulose (HEC). A CMCNa/HEC weight ratio of between 0/1 and 5/1, preferably between 1/1 and 3/1, was observed to enable the synthesis of a polymer hydrogel having optimum absorption properties.

Examples relating to the synthesis of different polymer hydrogels according to the invention, differing from one another in the weight percent (wt %) of citric acid and in the composition of the polymeric precursor, are provided below.

Preparation of Polymer Hydrogel A:

in a beaker containing distilled water, sorbitol at a concentration of 4% by weight referred to the weight of distilled water was added and mixed until complete solubilisation, which occurred within a few minutes. The CMCNa and HEC polymers are added at a total concentration of 2% by weight referred to the weight of distilled water, with a CMCNa/HEC weight ratio of 3/1. Mixing proceeded until solubilisation of the whole quantity of polymer is achieved and the solution became clear. At this stage, citric acid at a concentration of 1% by weight referred to the weight of the precursor was added to the solution, whose viscosity had greatly increased. The solution thereby obtained was poured into a vessel and dried at 48° C. for 48 hours. During this process, the macromolecules are stabilised into a polymeric network which is the backbone of the polymer hydrogel. At the end of the cross-linking process, the polymer hydrogel was washed with distilled water for 24 hours at room temperature. During this phase, the polymer hydrogel swelled up thereby eliminating the impurities. In order to obtain the maximum swelling degree and elimination of all of the impurities, at least 3 rinses with distilled water were performed during the 24 hours washing step. At the end of this washing step, the polymer hydrogel was dried by phase inversion in acetone as the nonsolvent, until a glassy white precipitate is obtained. The precipitate is then placed into an oven at 45° C. for about 3 hours, to remove any residual trace of acetone.

Preparation of Polymer Hydrogel B:

Polymer hydrogel B was prepared as polymer hydrogel A, with the only exception that the polymer is made only of CMCNa, and that the CMCNa concentration is 2% by weight referred to the weight of distilled water.

Preparation of Polymer Hydrogel C:

Polymer hydrogel C was prepared as polymer hydrogel B, with the only exception that the citric acid concentration is 2% by weight referred to the weight of CMCNa.

Preparation of Polymer Hydrogel D:

Polymer hydrogel D was prepared as polymer hydrogel B, with the only exception that the citric acid concentration is 0.5% by weight referred to the weight of CMCNa.

Absorption Measurements

In order to test the absorption properties of the polymer hydrogels prepared as described above, they were subjected to absorption measurements in distilled water. The absorption measurements essentially consist of placing the dry sample, obtained from the drying step, in distilled water, so that it swells up until an equilibrium condition is reached.

The absorption properties of the gel are assessed based on its swelling ratio (SR), defined according to the formula illustrated above. In order to minimise the influence of experimental errors, each test was performed on three samples from each gel, and then the mean value of the results of the three measurements was taken as the effective value.

Three dry samples were taken from each of the test gels, each having different weights and sizes. After recording the weights, the samples were swollen in abundant quantities of distilled water at room temperature. Upon reaching equilibrium after 24 hours, the samples were weighed once more in order to determine the swelling ratio.

Results

Table 2 below reports some of the results obtained, in terms of the swelling ratio, varying the concentrations of the reagents and the cross-linking times (6 hours, 13 hours, 18 hours, 24 hours).

TABLE 2

| Sample | CMCNa 75% | HEC 25% | CA | sorbitol | cross-linking time/ swelling ratio | | | |
|---|---|---|---|---|---|---|---|---|
| | | | | | 6 hours | 13 hours | 18 hours | 24 hours |
| g16 | 2% | 1% | 4% | | nr | 50 | 30 | 20 |
| g17 | 4% | 1% | 4% | | nr | 25 | 10 | 5 | nr = not cross-linked

It is pointed out that the increase in the polymer concentration exerts a negative effect on the swelling properties of the final product and it is also pointed out that the cross-linking time exerts a significant effect of the absorbing properties.

Thus, further experiments were carried out maintaining the polymer concentration fixed at 2% and varying the citric acid concentration. The results are reported in Table 3.

TABLE 3

| Sample | CMCNa 75% | HEC 25% | CA | sorbitol | cross-linking time/ swelling ratio | | | |
|---|---|---|---|---|---|---|---|---|
| | | | | | 6 hours | 13 hours | 18 hours | 24 hours |
| g21 | 2% | 2% | 4% | | 40 | 25 | 20 | 10 |
| g22 | 2% | 1% | 4% | | nr | 50 | 30 | 20 |
| g23 | 2% | 0.5% | 4% | | nr | Nr | 50 | 30 | nr = not cross-linked

Table 3 shows that the sample having the best swelling ratio is the sample designated as g22, which is characterised by a citric acid (CA) concentration of 1%.

Thus, further experiments were performed removing completely HEC from the solution. This should render the polymer hydrogel more hydrophilic thereby leading to an increase of the swelling ratio. Table 4 shows some of the results obtained.

TABLE 4

| Sample | CMCNa 100% | HEC 0% | CA | sorbitol | cross-linking time/ swelling ratio | | | |
|---|---|---|---|---|---|---|---|---|
| | | | | | 6 hours | 13 hours | 18 hours | 24 hours |
| g30 | 2% | 2% | 4% | | nr | 85 | 55 | 30 |
| g31 | 2% | 1% | 4% | | nr | 100 | 75 | 40 |
| g32 | 2% | 0.5% | 4% | | nr | Nr | 70 | 50 | nr = not cross-linked

The highest swelling ratio is associated with a cross-linking time of 13 hours and a citric acid concentration of 1%. It is also to be noticed that higher citric acid concentrations together with shorter cross-linking times lead to equally satisfactory swelling ratios, although the reaction is very fast and less easy to control.

Finally, the possibility of increasing the swelling ratio by creating porosity into the material which could promote the absorbing properties, was evaluated. For that purpose, the sample g31, subjected to cross-linking for 12 hours, was swelled into distilled water for 24 hours and then dried by phase inversion in acetone. With this technique, a swelling ratio of 200 was obtained.

Example 3

Swelling of a Polymer Hydrogel in Simulated Gastric Fluid (SGF) and SGF/Water Mixtures This example describes an evaluation of the superabsorbent polymer hydrogel denoted polymer hydrogel B in Example 2 in in vitro swelling and collapsing experiments in various media at 37° C.

Swelling Kinetics (in 100% SGF) at 37° C.

100 mg of the dried polymer hydrogel was immersed in either simulated gastric fluid ("SGF") or a mixture of SGF and water and allowed to swell until an equilibrium condition was reached. SGF was prepared according to USP Test Solutions procedures. The swelling ratio in each fluid was determined at various time points. The results are set forth in Tables 5 and 6.

TABLE 5

Swelling of dry polymer hydrogel B in 100% SGF at 37° C. The weights were recorded at 15, 30, 60 and 90 min.

| Swelling Time, min | Swelling Ratio, g/g |
|---|---|
| 15 | 15.4 |
| 30 | 15.6 |
| 60 | 16.2 |
| 90 | 15.1 |

TABLE 6

Swelling of Dry Polymer hydrogel B in a mixture of SGF and Water (1:8) at 37° C. The weights were recorded at 15, 30, 60 and 90 min.

| Sweling Time, min | Swelling Ratio, g/g |
|---|---|
| 15 | 78.8 |
| 30 | 84.6 |
| 60 | 88.6 |
| 90 | 79.3 |

Collapsing Kinetics (with Addition of SGF) at 37° C.

To simulate the effect of digestion on a hydrated polymer hydrogel, to the swollen polymer hydrogel from above (Table 6, SGF/water) after 60 minutes, 100% SGF was slowly added to collapse the gel particles. Swelling ratio was monitored as a function of cumulative volume of added SGF. The results are set forth in Table 7.

TABLE 7

| SGF added (mL) | Swelling Ratio (g/g) |
|---|---|
| 0 | 88.6 |
| 8 | 23.1 |
| 30 | 22.6 |
| 50 | 23.1 |
| 75 | 17.1 |

Kinetics of Swelling (in 1:8 SGF/Water), Collapsing (in SGF) and Re-Swelling (in Simulated Intestinal Fluid)

Experiments were conducted by monitoring the swelling ratio through a full cycle of swelling in 1:8 SGF/water, collapsing in SGF, and re-swelling (then degradation) in simulated intestinal fluid (SIF), all at 37° C. Experiments performed and results are provided in Table 8, for the re-swelling/degradation kinetics. pH values are given when available.

TABLE 8

Kinetics of swelling in SGF/water, collapsing in SGF, and re-swelling in SIF

| Expt. # | 60-min Swell in SGF/water Swell Ratio | Collapse in 70-mL SGF Swell Ratio | Re-swelling/Degradation in SIF | | | |
|---|---|---|---|---|---|---|
| | | | 30 min | 45 min | 90 min | 120 min |
| 1 | 95.5 pH 4.82 | 20.7 pH 1.76 | | | 71.2 | 87.3 |
| 2 | 95.3 | 19.5 pH 1.75 | 72.6 | | | 80.5 |

Conclusions:

This polymer hydrogel swells in simulated gastric fluids (pH 1.5) approximately 15 fold, and in a simulated gastric fluids/water mixture (pH 3) approximately 85 fold. This indicates that the polymer hydrogel has a pH/swelling correlation where at pH below 3 (pKa of CMC is ~3.1) there will be limited swelling of the polymer hydrogel due to absence of the Donnan effect. The polymer can also swell in the increased pH of simulated intestinal fluid.

Example 4

Effect of Polymer Hydrogel on Rat Feeding Behavior

A series of experiments was conducted to assess the effect of polymer hydrogel B in laboratory animals. One objective of these studies was to determine the effect of polymer hydrogel B on food intake in rats. The study was conducted in male Sprague Dawley rats, by acute administration of pre-swollen polymer hydrogel B by oral gavage A total of 22 male Sprague-Dawley rats were randomized into two weight-matched groups prior to polymer hydrogel or vehicle administration (the polymer hydrogel B was pre-swollen in water, 100 mg in 10 mL water). Food and water intake (digital balance) as well as locomotor activity (consecutive beam brakes) were monitored online every 5 minutes for 40 hours post dosing. Food and water intake data were collected using MaNi FeedWin, an online computerized feeding system using digital weighing cells. Two types of baseline food intake (digital balance) and lick counts were monitored. All data was entered into Excel spread-sheets and subsequently subjected to relevant statistical analyses Results are presented as mean±SEM unless otherwise stated. Statistical evaluation of the data is carried out using one-way or two-way analysis of variance (ANOVA).

Results and Conclusions

Figure 2:
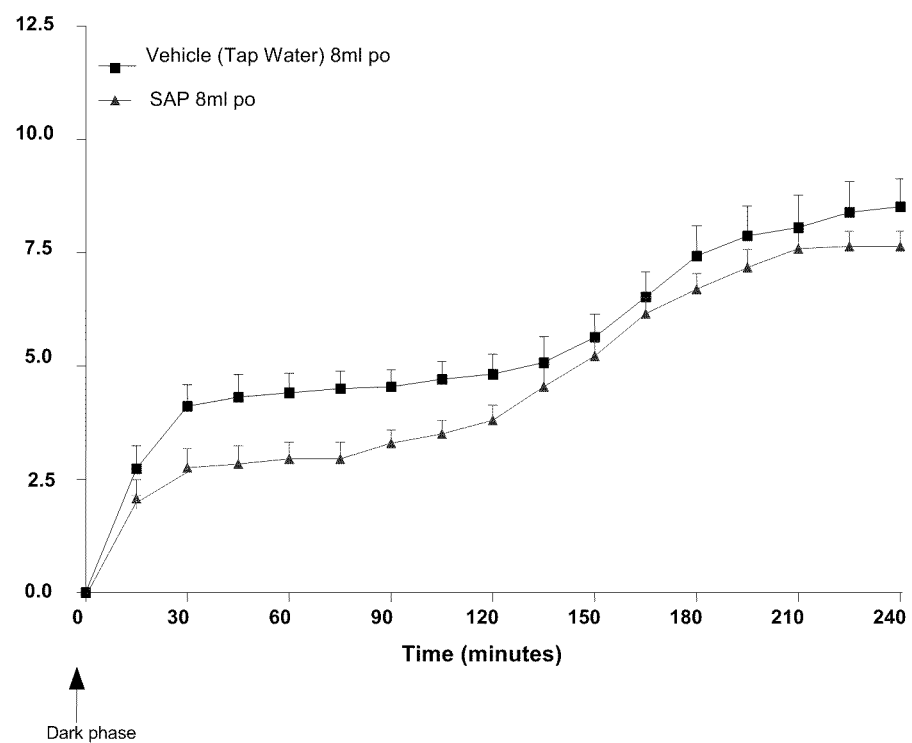
FIG. 2 is a graph of cumulative food intake as a function of time for rats administered a polymer hydrogel of the invention orally and rats administered vehicle only.

FIG. 2, a graph of cumulative food intake as a function of time, represents a typical study result. There was no difference between the groups at base line. Gavage of 8 mL of polymer hydrogel B induced satiety in the rats that led to a significant decrease in food intake. As shown in the yellow line, this polymer hydrogel induced a marked decrease in food intake that persisted over 2 hours. These data suggest that polymer hydrogel B can induce satiety in animals and leads to a decrease in food intake.

REFERENCES

[1] Anbergen U, Opperman W, Polymer, 31, 1854 (1990).
[2] Esposito F et al., J Appl Polym Sci, 60, 2403 (1996).
[3] Denn W L, Ferguson G N, U.S. Pat. No. 3,589,364, 1971.
[4] Sachetto J P et al., ES 484964, 1978.
[5] Choi Y S et al., Biomaterials, 20, 409 (1999).
[6] International patent application WO 2006/070337.
[7] Glusker J P. Acc. Chem. Res. 1980; 13:345-352.
[8] Wang C C et al., Applied Catalysis A: General 2005; 293:171-179.
[9] Coma V et al., Carbohydrate Polymers 2003; 51:265-271.
[10] Xie X S et al., Food Research International 2006; 39:332-341.
[11] Yang C Q et al., J. Appl. Polym. Sci. 1998; 70:2711-2718.
[12] Flory P. J., Principles of Polymer Chemistry, Ithaca, N.Y.: Cornell University Press, 1953.
[13] Sannino A. et al., Polymer 2005; 46:4676.
[14] Silverstein R. M., et al. Spectrometric Identification of Organic Compounds, Wiley, 1991, pp 120-130.
[15] Peppas N A, Polymer hydrogels in Medicine and Pharmacy; CRC Press, Boca Raton, Fla., 1987, p. 29.

[16] Chen CC and Wang CC, J. Sol-Gel Sci. Technol. 2006, 40: 31.
[17] Xie XS and Liu Q, Starch 2004, 56:364.
[18] Khutoyanskaya O V et al., Macromol. Chem. Phys. 2005, 206:1497.

What is claimed is:

1. A method of treating obesity in a subject in need thereof, comprising the step of orally administering to the subject a therapeutically effective amount of a polymer hydrogel comprising carboxymethylcellulose covalently cross-linked with citric acid.

2. The method of claim 1, wherein the polymer hydrogel further comprises a nonionic hydrophilic polymer.

3. The method of claim 2, wherein the nonionic polymer is hydroxyethylcellulose.

4. The method of claim 3, wherein the weight ratio of carboxymethylcellulose to hydroxyethylcellulose is about 3.

5. The method of claim 1 wherein the polymer hydrogel consists essentially of carboxymethylcellulose covalently crosslinked with citric acid.

6. The method of claim 1, wherein the polymer hydrogel can absorb at least about 30 times its dry weight of simulated gastric fluid/water (1/8).

7. The method of claim 6, wherein the polymer hydrogel can absorb at least about 50 times its dry weight of simulated gastric fluid/water (1/8).

8. The method of claim 7, wherein the polymer hydrogel can absorb at least about 80 times its dry weight of simulated gastric fluid/water (1/8).

9. The method of claim 1, wherein the weight ratio of citric acid to carboxymethylcellulose is about 1% to about 5%.

10. The method of claim 1, wherein the polymer hydrogel is substantially dry.

11. A method of reducing calorie intake by a subject in need thereof, comprising the step of orally administering to the subject an effective amount of a polymer hydrogel comprising carboxymethylcellulose covalently cross-linked with citric acid.

12. The method of claim 11, wherein the polymer hydrogel further comprises a nonionic hydrophilic polymer.

13. The method of claim 12, wherein the nonionic polymer is hydroxyethylcellulose.

14. The method of claim 13, wherein the weight ratio of carboxymethylcellulose to hydroxyethylcellulose is about 3.

15. The method of claim 11, wherein the polymer hydrogel consists essentially of carboxymethylcellulose covalently crosslinked with citric acid.

16. The method of claim 11, wherein the polymer hydrogel can absorb at least about 30 times its dry weight of simulated gastric fluid/water (1/8).

17. The method of claim 16, wherein the polymer hydrogel can absorb at least about 50 times its dry weight of simulated gastric fluid/water (1/8).

18. The method of claim 17, wherein the polymer hydrogel can absorb at least about 80 times its dry weight of simulated gastric fluid/water (1/8).

19. The method of claim 11, wherein the weight ratio of citric acid to carboxymethylcellulose is about 1% to about 5%.

20. The method of claim 11, wherein the polymer hydrogel is substantially dry.

* * * * *